US00PP11952P2

(12) United States Plant Patent
Bradford

(10) Patent No.: US PP11,952 P2
(45) Date of Patent: Jun. 19, 2001

(54) NECTARINE TREE NAMED 'RUBY BRIGHT'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 09/472,307

(22) Filed: Dec. 27, 1999

(51) Int. Cl.[7] ..... A01H 5/00
(52) U.S. Cl. ..... Plt./190
(58) Field of Search ..... Plt./190

(56) References Cited

U.S. PATENT DOCUMENTS

P.P. 7,193 3/1990 Bradford et al. ..... Plt./190
P.P. 7,507 4/1991 Bradford et al. ..... Plt./190

*Primary Examiner*—Bruce R. Campell
*Assistant Examiner*—Wendy A Baker

(57) ABSTRACT

The present invention relates to a nectarine tree, *Prunus persica,* and more particularly to a new and distinct variety broadly characterized by a medium sized, vigorous, self-fertile, productive and regular bearing tree. The fruit matures under the ecological conditions described approximately the second week in July, with first picking on Jul. 15, 1999. The fruit is uniformly large in size, acidic and sweet in flavor, globose in shape, clingstone in type, firm and crisp in texture, and fully red in skin color. The variety was a first generation cross using Red Glen (U.S. Plant Pat. No. 7,193) nectarine as the seed parent and Spring Bright (U.S. Plant Pat. No. 7,507) as the selected pollen parent.

1 Drawing Sheet

BACKGROUND OF THE VARIETY

In a continuing effort to improve the quality of fresh market and shipping fruits, I, the inventor, typically hybridize a large number of nectarine and peach seedlings each year. The present invention relates to a new and distinct variety of nectarine tree (*Prunus persica*), which has been denominated varietally as 'Ruby Bright'. The present variety was hybridized in 1993, grown as a seedling on its own root in the greenhouse, and transplanted to a cultivated area of my experimental orchard at Bradford Farms near Le Grand, Calif. in Merced County (San Joaquin Valley). It was developed as a first generation cross using Red Glen (U.S. Plant Pat. No. 7,193) nectarine as the seed parent and Spring Bright (U.S. Plant Pat. No. 7,507) as the selected pollen parent. Subsequent to origination of the present variety of nectarine tree, I asexually reproduced it by budding and grafting, in the experimental orchard described above, and such reproduction of plant and fruit characteristics were true to the original plant in all respects. The reproduction of the variety included the use of Nemaguard Rootstock (unpatented), the standard of the stone fruit industry in central California, upon which the present variety was compatible and true to type.

The present variety is most similar to its pollen parent Spring Bright (U.S. Plant Pat. No. 7,507) nectarine, by producing fruit that is full red in skin color, yellow in flesh color, clingstone in type and firm in texture, but is distinguished therefrom and an improvement thereon by having reniform instead of globose glands and by producing fruit that matures about ten days later.

The present variety is similar to its seed parent, Red Glen (U.S. Plant Pat. No. 7,193) nectarine, by producing firm, full red, yellow flesh, clingstone nectarines, but is distinguished therefrom by producing fruit that ripens about 22 days earlier and has much less red flesh mottling next to the stone.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed of a 5 year-old tree grown under the ecological conditions prevailing near Le Grand, Merced County (San Joaquin Valley), Calif., and was developed at the state of hard shipping ripe on Jul. 18, 1999. However, during 1999 most stone fruit varieties in California ripened approximately ten days later than normal. All major color code designations are by reference to the Inter-Society Color Council, National Bureau of Standards. Common color names are also used occasionally.

TREE

Size: Medium, reaching and maintaining a height of 10' [3.05 meters] after the 5th growing season utilizing typical dormant pruning.

Vigor: Vigorous, responding typically to irrigation and fertilization. The plant should be grown on a standard commercial rootstock for production purposes. The variety grows about 3' [0.91 meters] of surplus top-growth during the spring and summer.

Growth: Upright and dense.

Form: Vase formed.

Hardiness: Hardy with respect to typical central California winters.

Production: Productive, thinning required.

Fertility: Self-fertile.

Bearing: Regular bearer, with no alternate bearing observed.

Trunk:

*Size.*—Medium, reaching a maximum diameter of 5" [127 mm.] after 5 growing seasons.

*Texture.*—Somewhat shaggy.

*Bark color.*—Grayish brown [61. gy.Br].

*Lenticels.*—Numerous. Color: Moderate orange yellow [71. m.OY]. Typical Size: ⅛" to 7/16" [3.2–11.1 mm.].

Branches:

*Size.*—Medium, typical of *Prunus persica.*

*Texture.*—Smooth on 1st year wood, increasing roughness with age.

*Color.*—1st Year Wood Topside: Grayish red [19. gy.R]. 1st Year Wood Underside: Brilliant yellow green [116. brill.YG]. Older Wood: Dark yellowish brown [78. d.yBr].

*Lenticels.*—Numerous, small. Color: Dark orange yellow [72. d.OY]. Size: 1/16" to 3/16" [1.6–4.8 mm.].

Leaves:

*Size.*—Large. Average Length: 6⅛" [155.6 mm.]. Average Width: 1 7/16" [36.5 mm.].

*Thickness.*—Medium.

*Form.*—Elliptical.

*Apex.*—Acuminate.

*Base.*—Acute.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: 7/16" [11.1 mm.]. Average Thickness: 1/16" [1.6 mm.]. Color: Light yellow green [119. l.YG].

*Stipules.*—2 per leaf bud, up to 6 at the growing tip. Average Length: ⅜" [9.5 mm.].

*Glands.*—Numbers: 1 to 4, but mostly 2, per leaf. Position: Alternately positioned on petiole and base of blade. Size: Medium. Form: Reniform. Color: Light yellow green [119. l.YG].

Flower buds:

*Hardiness.*—Hardy with respect to central California winters.

*Diameter.*—Typically ⅜" [9.5 mm.] 1 week before bloom.

*Length.*—Typically ¾" [19.1 mm.] 1 week before bloom.

*Form.*—Not appressed.

*Color.*—Brilliant purplish pink [246. brill. p. Pk.].

*Surface.*—Pubescent.

Flowers: Perfect, complete, perigynous, usually a single pistil, typically thirty or more stamens, five sepals and petal locations alternately positioned.

*Blooming period.*—Medium as compared with other varieties.

*Onset of bloom.*—One percent on Mar. 3, 1999.

*Duration of bloom.*—One to two weeks, dependent on ambient temperature.

*Type.*—Showy.

*Number of petals.*—Usually five, some doubles.

*Number per cluster.*—Generally from 1 to 3.

*Petal shape.*—Rounded.

*Petal margin.*—Slightly wavy.

*Average petal diameter.*—11/16" [17.5 mm.].

*Petal color.*—Pale purplish pink [252. p.pPk].

*Anther color.*—Moderate red [15. m.R] when first opened.

*Average pistil length.*—¾" [19.1 mm.].

*Fragrance.*—Strong when nectar is present.

*Average diameter.*—1⅞" [47.6 mm.].

FRUIT

Maturity when described: Hard shipping ripe, Jul. 18, 1999, noting the 1999 ripening season was delayed about ten days later than normal.

Date of first picking: Jul. 15, 1999.

Date of last picking: Jul. 27, 1999.

Size: Uniform, large.

*Average diameter axially.*—2¾" [69.9 mm.].

*Average diameter across suture plane.*—2¾" [69.9 mm.].

*Typical weight.*—6.70 ounces [190 grams].

Form: Globose, uniform, mostly symmetrical.

*Longitudinal section form.*—Round.

*Transverse section through diameter.*—Round.

Suture: A sharp crack near the stem becoming an inconspicuous line on the lateral surface transforming into a shallow groove toward the apex with a depression beyond the pistil point.

Ventral surface: Rounded.

Lips: Slightly unequal.

Cavity: Flaring, circular, suture showing on one side, stem markings typical.

*Depth.*—7/16" [11.1 mm.].

*Breadth.*—15/16" [23.8 mm.].

Base: Rounded to somewhat truncate.

Apex: Rounded to slightly truncate.

Pistil point: Both apical and oblique, negligible in length, depressed within the suture.

Stem: Medium.

*Average length.*—⅜" [9.5 mm.].

*Average width.*—3/16" [4.8 mm.].

Skin:

*Thickness.*—Medium.

*Texture.*—Medium.

*Tenacity.*—Tenacious to flesh.

*Tendency to crack.*—None observed.

*Color.*—Very dark red [17. v.d.R] smoothly blending into deep reddish orange [36. deep rO], with a minor amount of deep orange yellow [69. deep OY] freckling.

Flesh:

*Color.*—Brilliant yellow [83. brill.Y] with a little dark red [16. d.R] flecking concentrated midway between the stone and skin.

*Surface of pit cavity.*—Brilliant yellow [83. brill.Y] with a tinge of moderate red [15. m.R] fibers breaking when twisted away from the stone.

*Amygdalin.*—Moderate.

*Juice.*—Abundant, rich.

*Texture.*—Firm, crisp.

*Fibers.*—Abundant, fine.

*Ripens.*—Earliest at the apex and along the lips.

*Flavor.*—Acidic and sweet, typically 13 brix.

*Aroma.*—Moderate.

*Eating quality.*—Excellent.

STONE

Type: Clingstone.

Form: Oval.

Base: Straight.

Apex: Acute.

Hilum: Narrow.

Sides: Slightly unequal.

Surface: Irregularly furrowed toward the apex, pitted toward the base.

Ridges: Jagged toward the base.

Color: Moderate yellowish brown [77. m.yBr] when first removed from fruit.

Pit wall: ¼" [6.4 mm.] thick.

Tendency to split: Slight.

Kernel:

*Form.*—Oval.

*Taste.*—Sweet.

*Viable.*—Yes.

*Average width.*—17/32" [13.5 mm.].

*Average length.*—¾" [19.1 mm.].

*Pellicle color.*—Light grayish brown [60. l.gy.Br].

*Skin color.*—Pale yellow [89. p.Y] with light grayish brown [60. l.gy.Br] veins when first removed from stone.

*Amygdalin.*—Scant.

USE

Market: Fresh and long distance shipping.

Keeping quality: Fruit quality observed to remain in good condition in excess of 17 days in cold room at 36° Fahrenheit [2° Celsius].

Resistance to insects: No unusual susceptibilities noted.

Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to its pollen parent Spring Bright (U.S. Plant Pat. No. 7,507) nectarine, by producing fruit that is full red in skin color, yellow in flesh color, clingstone in type and firm in texture, but is distinguished therefrom and an improvement thereon by having reniform instead of globose glands and by producing fruit that matures about ten days later.

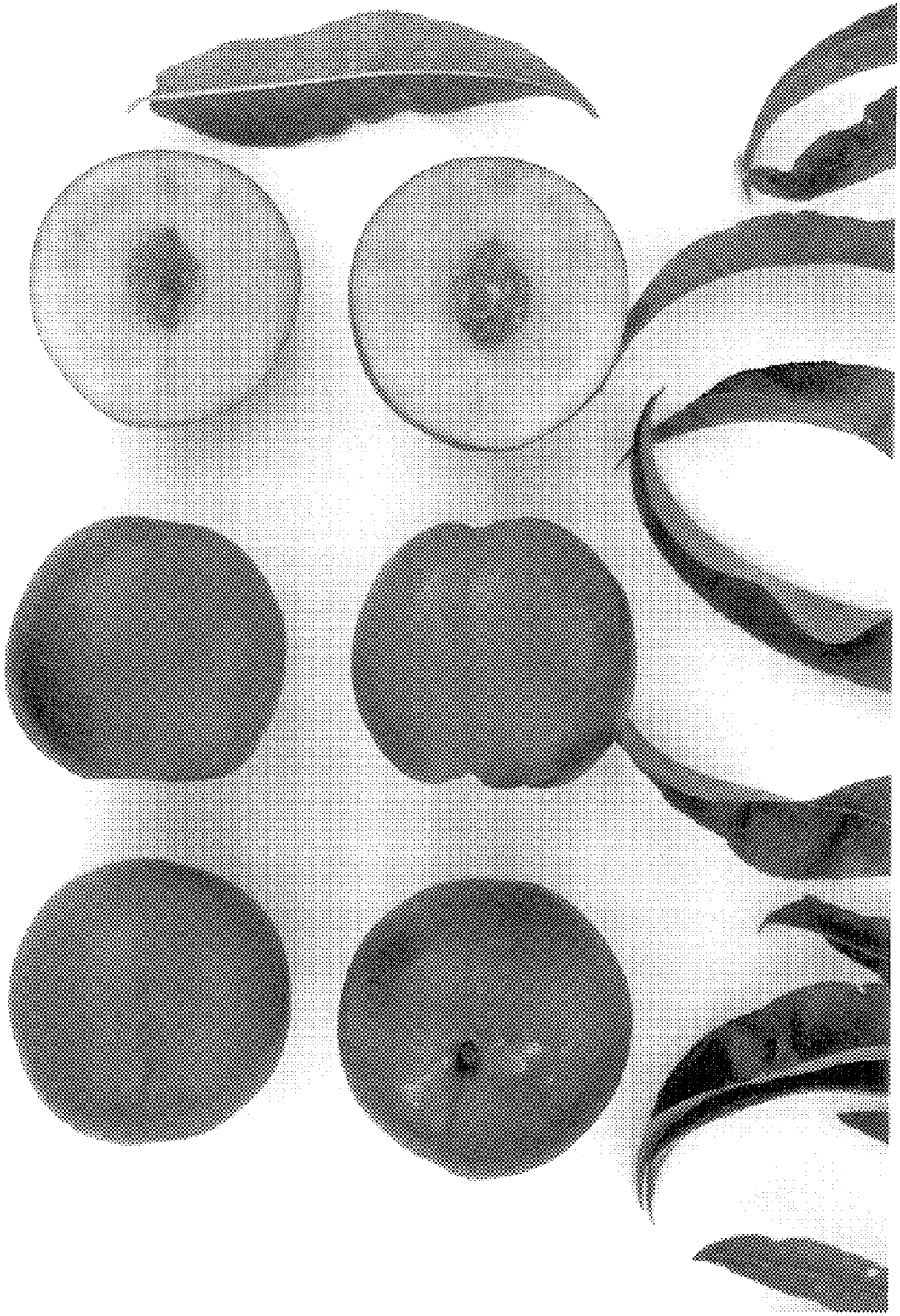

* * * * *